(12) United States Patent
Hulaj

(10) Patent No.: US 11,180,444 B2
(45) Date of Patent: Nov. 23, 2021

(54) POLYIMINO KETOALDEHYDES

(71) Applicant: NOVUM SPERO LTD., Zagreb (HR)

(72) Inventor: Besim Hulaj, Zagreb (HR)

(73) Assignee: NOVUM SPERO LTD, Zagreb (HR)

( * ) Notice: Subject to any disclaimer, the term of this patent is extended or adjusted under 35 U.S.C. 154(b) by 0 days.

(21) Appl. No.: 16/487,162

(22) PCT Filed: Feb. 21, 2017

(86) PCT No.: PCT/HR2017/000002
§ 371 (c)(1),
(2) Date: Aug. 20, 2019

(87) PCT Pub. No.: WO2018/154344
PCT Pub. Date: Aug. 30, 2018

(65) Prior Publication Data
US 2020/0062697 A1    Feb. 27, 2020

(51) Int. Cl.
*C07C 251/08* (2006.01)
*A61P 31/08* (2006.01)
*A61P 31/04* (2006.01)
*A61P 31/06* (2006.01)

(52) U.S. Cl.
CPC ............ *C07C 251/08* (2013.01); *A61P 31/04* (2018.01); *A61P 31/06* (2018.01); *A61P 31/08* (2018.01)

(58) Field of Classification Search
CPC ........ C07C 251/08; A61P 31/08; A61P 31/04; A61P 31/06
See application file for complete search history.

(56) References Cited

PUBLICATIONS

Chemical Abstract Service, STN Registry Database (online), Registry No. 1081748-84-6 [Entered STN: Dec. 8, 2008]. (Year: 2008).*
Jinbing Liu et al, "Synthesis and antibacterial activities of para-alkoxy phenyl-[beta]-ketoaldehyde derivatives", Medicinal Chemistry Research., vol. 22, No. 9, Jan. 3, 2013 (Jan. 3, 2013), p. 4228-4238.

* cited by examiner

*Primary Examiner* — Amanda L. Aguirre
(74) *Attorney, Agent, or Firm* — Daniel P. Burke & Associates, PLLC; Daniel P. Burke; Georgia Damoulakis

(57) ABSTRACT

The compounds with the general formula I are disclosed

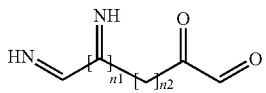

where $n_1$ is the number of carbon atoms connected to nitrogen atom by a double bond and can take on values of 25 to 41, and where $n_2$ is the number of —$CH_2$— groups and can take on values of 15 to 23, as well as their biologically acceptable salts and solvates.

19 Claims, 1 Drawing Sheet

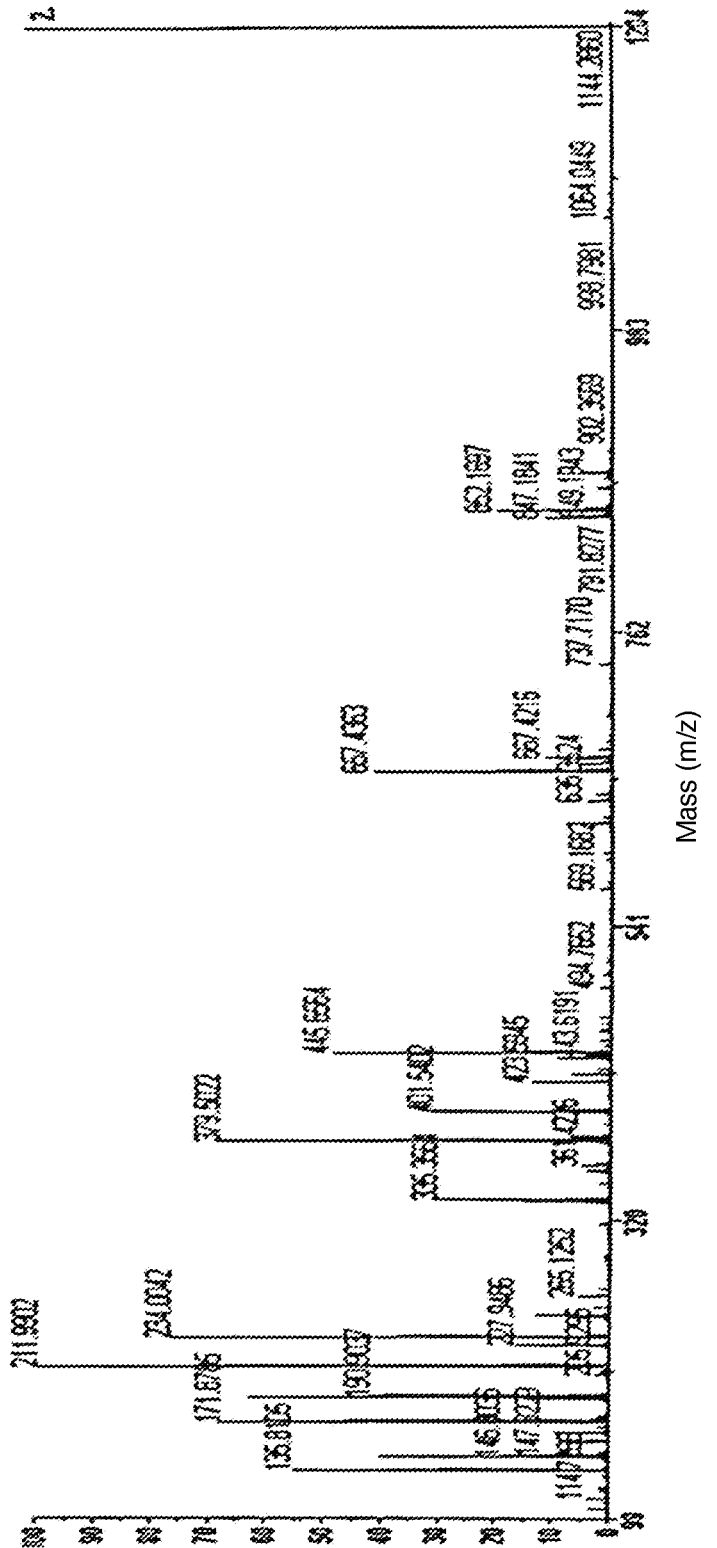

POLYIMINO KETOALDEHYDES

Present invention refers to the new biologically active polyimino ketoaldehyde compounds and their antibacterial properties, pharmaceutical preparations containing compounds of poly(imino) ketoaldehydes as an active substance, their use in the treatment of bacterial infections and their preparation process.

Polyimino ketoaldehydes are, according to the present invention, compounds with general formula I:

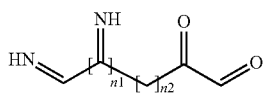

where $n_1$ is the number of carbon atoms connected to nitrogen atom by a double bond and can take values of 25 to 41, and where $n_2$ is the number of —$CH_2$— groups and can take values of 15 to 23, as well as their biologically acceptable salts and solvates.

In one of the variants of the invention, $n_1$ can take values 25, 33, or 41, and $n_2$ can take values 15, 19, or 23, as well as their biologically acceptable salts and/or solvates.

In particular, the present invention relates to the compound with the formula:

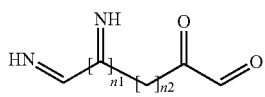

where $n_1$ has a value of 33, and $n_2$ a value of 19. The chemical name of the compound in which $n_1=33$, and $n_2=19$ is 1-amino-tetratriacontyl-henicosa-20-on-21-al, and it is referred to as Varoxicilin.

In order to obtain the compound according to the subject invention, a biotransformation of substrate with enzymes was performed in which the substrate can be selected from the group consisting of glycine, L-alanine, L-valine, L-leucine, 2-aminobutyric acid, 4-metil-theonin and D-alanine, whereas the enzyme is selected from a group consisting of cyclosporine-A synthetase (hereinafter: cAs), nonribosomal peptide synthetase 1 (hereinafter: NRPS1).

The biotransformation itself occurs in the following phases:
1. Substrate activation to form an adenylate (ATP) at the adenylation domain of the enzyme.
2. Esterification of the activated amino acid with thiol group of pantothenic residues, by which the aminoacyl group is transferred to the thiolation domain of the enzyme and a corresponding thioester is created.

In an acidic medium, the esterified amino acids are joined together in a way that results in the creation of a compound with general formula I.

Hence, regardless of the substrate used, the adenylade domain forms acyl-adenylate substrate which uses a covalent bond to join substrate molecule to phosphopantetheine thus forming a cross-linked thioester which further transforms into a compound with general formula I, in particular 1-amino-tetratriacontyl-henicosa-20-on-21-al in the form of white precipitate which is purified by alternate washing in acid and water.

In order to obtain a compound with general formula I, apart from substrates and enzymes, one also needs adenosine triphosphate (ATP) and cofactors. $Mg^{2+}$ was used as a cofactor. The cofactor is added in the reaction mixture in the form of magnesium sulphate with halogen or chalcogen elements. In addition, a buffer for the suspension of enzymes is also necessary, which is used for keeping the pH level of the reaction mixture within the neutral range, i.e. within a pH range between 6 and 7. The appropriate buffer is any buffer that maintains the pH value within the stated range, for example acetate buffer. The reaction for obtaining the compound with general formula I is performed in the manner that the buffered components of reaction mixture consisting of $Mg^{2+}$, ATP and substrates are mixed in the acetate buffer in a reactor, and the reaction is initiated by adding the enzyme suspension to the buffer. The reaction is performed at room temperature, i.e. at a temperature between 18° C. and 30° C. or, ideally, between 23° C. and 28° C. The preferred temperature for the execution of the procedure for obtaining a compound with general formula I is 27° C. pH value is continuously measured with a pH meter and, if necessary, maintained at optimal pH conditions with bases such as water solution of NaOH. The reaction is stopped with acid water solution, after which the reaction mixture cools down. During the cooling period, a white precipitate is formed which is washed with acid and water alternately.

The second aspect of the invention concerns the pharmaceutical composition which contains an active amount of the compound with general formula I or its pharmaceutically acceptable salts and solvates in pharmaceutical variant that is appropriate for parenteral use, oral administration and intravenous use. Apart from the active compound, according to the subject invention, the pharmaceutical composition can contain one or more pharmaceutically acceptable excipients such as carriers, lubricants, glidants, dyes, fillers, i.e. binders, disintegrants and surfactants.

In case of pharmaceutical variant for oral administration, the pharmaceutical preparation can be compressed to give pellets, granules, tablets, blisters, capsules, tablets with controlled release of active substance. All pharmaceutical preparations, apart from the active substance, can contain pharmaceutically acceptable excipients. Excipients can be selected from a group of carriers, binders, fillers, surfactants, disintegrants, glidants, lubricants and other known pharmaceutically acceptable excipients.

Carriers are selected from a group of known pharmaceutically acceptable carriers such as protein nanoparticles, polypeptides, liposomes, polymeric micelles, microspheres and mixtures of two or more known carriers. The above examples of carriers are for illustrative purposes only and the selection of carriers is in no way limited to the above examples or their mixtures.

Binders—fillers are selected from a group of known pharmaceutically acceptable binders-fillers such as sucrose, lactose, starch, cellulose, mannitol, sorbitol, xylitol, microcrystalline cellulose, siliconized microcrystalline cellulose, calcium hydrogen phosphate, calcium carbonate, calcium lactate and mixtures of two or more known pharmaceutically acceptable binders-fillers. The above examples of binders-fillers are for illustrative purposes only and the selection of binders-fillers is in no way limited to the above examples or their mixtures.

Surfactants are selected from a group of known pharmaceutically acceptable surfactants such as fatty acid esters, polysorbates, polyoxyethylene alkyl ethers, polyoxamers, triglycerides, polyoxylglycerides or mixtures of two or more known pharmaceutically acceptable surfactants. The above examples of surfactants are for illustrative purposes only and the selection of surfactants is in no way limited to the above examples or their mixtures.

Disintegrants are selected from a group of known pharmaceutically acceptable disintegrants such as cross-linked polymers, for example carboxymethyl cellulose, polyvinylpyrrolidone or mixtures thereof. The above examples of disintegrants are for illustrative purposes only and the selection of disintegrants is in no way limited to the above examples or their mixtures.

Glidants and lubricants are selected from a group of pharmaceutically known glidants and lubricants such as talc, silica powder, magnesium carbonate, magnesium stearate, or a mixture of two or more known pharmaceutically acceptable glidants and lubricant. The above examples of glidants and lubricants are for illustrative purposes and the selection of glidants and lubricants is in no way limited to the above examples or their mixtures.

Pharmaceutical preparation according to the invention has the following composition:

| | |
|---|---|
| 1. a compound with general formula I | 40% w/w until 60% w/w |
| 2. excipients | 40% w/w until 60% |

The figure is a mass spectra of a compound of one embodiment of the invention.

EXAMPLE 1—PREPARATION of 1-AMINO-TETRATRIACONTYL-HENICOSA-20-ON-21-AL 0.1 mol/L of acetate buffer is prepared by mixing 0.1 mol/L aqueous octenic acid solution with 0.1 mol/l aqueous NaOH solution. The resulting solution has a pH of 6.

NRPS1 suspension was prepared in acetate buffer. Final NRPS1 concentration in suspension amounted to 0.06 g/L.

0.51 g of glycine, 0.85 g of $MgCl_2$, 0.043 g of ATP was added to the reaction flask with magnetic stirrer and the mixture was dissolved in 85 mL of previously prepared acetate buffer. Reaction is initiated by adding 85 μL of NRPS1 suspension to the reaction flask. The temperature at which the reaction occurred was 27° C. The stirring rate of the magnetic stirrer amounted to 500 spins/min, and the reaction time was 120 min. The reaction was stopped by admixing 85 mL 7% v/v water solution of trichloroacetic acid (ratio of reaction mixture and acid is 1:1). The reaction vessel was then placed on ice for 30 minutes. After cooling, the process of evaporation on a rotating evaporator with water bath was initiated. After removal of water, additional drying on rotary evaporator with water bath with a temperature of 60° C. for more than one hour was conducted. 0.46 g of white precipitate—with temperature of 125° C. was obtained. The sample was dissolved in isopropanol and analysed with high-resolution mass spectrometry (ESI-qTOF) on Synapt G2-Si (Waters, USA). Mass spectres were recorded in positive and negative ion mode operation. The calculated peak was supposed to appear at 445.50 m/z, and the observed peak was at 445.6564 inferring that the characteristic peak for compound 1-amino-tetratriacontyl-henicosa-20-on-21-al is at 445.7959 with mass measurement error within the accuracy limits at 5 ppm—see picture 1.

EXAMPLE 2—COMPOSITION OF ORAL PREPARATION 500 mg of 1-Amino-Tetratriacontyl-Henicosa-20-on-21-al 500 mg of Excipients Excipients in this example are hypromellose, microcrystalline cellulose, dye, titanium dioxide.

The following invention aspect concerns antibacterial activity of the compound with general formula I

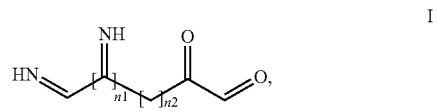

in particular antibacterial activity of 1-amino-tetratriacontyl-henicosa-20-on-21-al. In vitro testing showed that the compound with general formula I, as well as compound 1-1-amino-tetratriacontyl-henicosa-20-on-21-al, shows antibacterial properties against gram-positive and gram-negative bacteria including multi-resistant bacteria.

The compound with general formula I demonstrates antibacterial properties against the following bacteria: *Neisseria gonorrhoea, Acinetobacter baumannii, Staphylococcus aureus* (MRSA, *Burkholderia cepaci, Pseudomonas aeruginos, Clostridium difficil, Escherichia coli* (*E. coli* ESBL, *Mycobacterium tuberculosis, Klebsiella pneumoniae, Streptococcus pyogenes*. Table 1 shows inhibition zones for Avian Pathogenic *Escherichia coli* multi-resistant strain against 1-amino-tetratriacontyl-henicosa-20-on-21-al, Amoxicillin, Trimethoprim sulphate, tetracycline and Sulfadimidine.

As shown, only 1-amino-tetratriacontyl-henicosa-20-on-21-al has an effect on the inhibition of the stated strain of *E. Coli*.

Table 1 contains the results for inhibition diameter expressed in mm. Table 2 shows minimal concentration of 1-amino-tetratriacontyl-henicosa-20-on-21-al expressed in mg/mL that is necessary for the inhibition of Avian Pathogenic *Escherichia coli* multi-resistant strain. 1-amino-tetratriacontyl-henicosa-20-on-21-al is marked in tables as Cm. Antibiotics from Table 1 are administered in their standard dose for this type of testing. It is evident that only 1-amino-tetratriacontyl-henicosa-20-on-21-al shows inhibitory activity against Avian Pathogenic *Escherichia coli* multi-resistant strain.

TABLE 1

Inhibition zones of Avian Pathogenic *Escherichia coli* multi-resistant strain in mm

| Concentration | Inhibition zone |
|---|---|
| 20 μL of CM compound solution (350 μg/1 μL) per disc | 10 mm |
| 15 μL of CM compound solution (350 μg/1 μL) per disc | 9 mm |
| 10 μL of CM compound solution (350 μg/1 μL) per disc | 8 mm |
| Amoxicillin (25 μg per disc) | 0 mm |
| Trimethoprim sulphate (1.25 μg + 23.75 μg per disc) | 0 mm |
| Tetracycline (30 μg per disc) | 0 mm |
| Sulfadimidine (300 μg per disc) | 0 mm |

TABLE 2

Minimum inhibitory concentration of 1-amino-tetratriacontyl-henicosa-20-on-21-al necessary for inhibition of Avian Pathogenic *Escherichia coli* multi-resistant strain

| Concentration | Inhibition |
|---|---|
| 80 mg/1 ml | + |
| 8 mg/1 ml | + |
| 0.8 mg/1 ml | + |
| 0.08 mg/1 ml | − |

Given the results of in-vitro testing, the compounds with general formula I, especially 1-amino-tetratriacontyl-henicosa-20-on-21-al, represent medications, mainly medications against bacterial infections and are used in the treatment of bacterial infections. The bacterial infections that compounds with general formula I, especially 1-amino-tetratriacontyl-henicosa-20-on-21-al, successfully treat are: anthrax, bacterial meningitis, brucellosis, bubonic plague, diphtheria, epidemic typhus, gonorrhoea, whooping cough (pertussis), campylobacteriosis, chlamydia (trachoma), cholera, plague, legionellosis, leprosy (Hansen's disease), leptospirosis in humans, leptospirosis, listeriosis, Lyme disease, melioidosis, nocardiosis, pneumonia, relapsing fever, psittacosis, q fever, salmonella, syphilis, MRSA infection, scarlet fever, shigellosis, tetanus, typhus, typhoid fever, tuberculosis, tularemia, rat-bite fever.

The invention claimed is:

1. A compound with the general formula where $n_1$ is the number of carbon atoms connected to nitrogen atom by a double bond and can take values of 25 to 41, and where $n_2$ is the number of —$CH_2$— groups and can take values of 15 to 23, or a biologically acceptable salt or solvate thereof.

2. The compound according to claim 1, wherein $n_1$ is 25, 33, or 41, and $n_2$ is 15, 19, or 23.

3. The compound according to claim 2, wherein said compound is a 1-amino-tetratriacontyl-henicosa-20-on-21-al.

4. The compound according to claim 1, wherein said compound is a 1-amino-tetratriacontyl-henicosa-20-on-21-al.

5. A pharmaceutical preparation comprising a biologically effective concentration of a compound with the general formula where $n_1$ is the number of carbon atoms connected to nitrogen atom by a double bond and can take values of 25 to 41, and where $n_2$ is the number of —$CH_2$— groups and can take values of 15 to 23, or a pharmaceutically acceptable salt or solvate thereof.

6. A pharmaceutical preparation according to claim 5 wherein $n_1$ is 25, 33, or 41, and $n_2$ is 15, 19, or 23.

7. The pharmaceutical preparation according to claim 5, wherein said preparation comprises a biologically effective concentration of the compound 1-amino-tetratriacontyl-henicosa-20-on-21-al or a pharmaceutically acceptable salt or solvate thereof.

8. The pharmaceutical preparation according to claim 7, further comprising at least one pharmaceutically acceptable excipient.

9. The pharmaceutical preparation according to claim 5, further comprising at least one pharmaceutically acceptable excipient.

10. A compound with the general formula where $n_1$ is the number of carbon atoms connected to nitrogen atom by a double bond and can take values of 25 to 41, and where $n_2$ is the number of —$CH_2$— groups and can take values of 15 to 23, as a drug.

11. A compound according to claim 10 wherein $n_1$ is 25, 33, or 41, and $n_2$ is 15, 19, or 23.

12. A compound according to claim 10, wherein said compound is a 1-amino-tetratriacontyl-henicosa-20-on-21-al.

13. A compound according to claim 12 for treatment of anthrax, bacterial meningitis, brucellosis, bubonic plague, diphtheria, epidemic typhus, gonorrhoea, whooping cough (pertussis), campylobacteriosis, chlamydia, cholera, plague, legionellosis, leprosy (Hansen's disease), leptospirosis, listeriosis, Lyme disease, melioidosis, nocardiosis, pneumonia, relapsing fever, psittacosis, q fever, salmonella, syphilis, MRSA infection, scarlet fever, shigellosis, tetanus, typhus, typhoid fever, tuberculosis, tularemia, or rat-bite fever.

14. A compound according to claim 10, for treating a bacterial infection caused by gram-positive or gram-negative bacteria.

15. A compound according to claim 14 for treatment of anthrax, bacterial meningitis, brucellosis, bubonic plague, diphtheria, epidemic typhus, gonorrhoea, whooping cough (pertussis), campylobacteriosis, chlamydia, cholera, plague, legionellosis, leprosy (Hansen's disease), leptospirosis, listeriosis, Lyme disease, melioidosis, nocardiosis, pneumonia, relapsing fever, psittacosis, q fever, salmonella, syphilis, MRSA infection, scarlet fever, shigellosis, tetanus, typhus, typhoid fever, tuberculosis, tularemia, or rat-bite fever.

16. A method of treating a bacterial infection caused by gram-positive or gram negative bacteria comprising the step of administering an effective amount of a compound with the general formula where $n_1$ is the number of carbon atoms connected to nitrogen atom by a double bond and can take values of 25 to 41, and where $n_2$ is the number of —$CH_2$— groups and can take values of 15 to 23.

17. The method according to claim 16 wherein $n_1$ is 25, 33, or 41, and $n_2$ is 15, 19, or 23.

18. The method according to claim 16 wherein said compound is a 1-amino-tetratriacontyl-henicosa-20-on-21-al.

19. The method according to claim 16 wherein said bacterial infection is anthrax, bacterial meningitis, brucellosis, bubonic plague, diphtheria, epidemic typhus, gonorrhoea, whooping cough (pertussis), campylobacteriosis, chlamydia, cholera, plague, legionellosis, leprosy (Hansen's disease), leptospirosis, listeriosis, Lyme disease, melioidosis, nocardiosis, pneumonia, relapsing fever, psittacosis, q fever, salmonella, syphilis, MRSA infection, scarlet fever, shigellosis, tetanus, typhus, typhoid fever, tuberculosis, tularemia, or rat-bite fever.

* * * * *